US012805748B2

(12) United States Patent
Ing et al.

(10) Patent No.: US 12,805,748 B2
(45) Date of Patent: Nov. 24, 2026

(54) METHOD FOR CHARACTERIZING THE VIBRATION OF A SURFACE

(71) Applicants: CENTRE NATIONAL DE LA RECHERCHE SCIENTIFIQUE, Paris (FR); ECOLE SUPÉRIEURE DE PHYSIQUE ET DE CHIMIE INDUSTRIELLES DE LA VILLE DE PARIS, Paris (FR); SORBONNE UNIVERSITE, Paris (FR); INSTITUT NATIONAL DE LA SANTE ET DE LA RECHERCHE MEDICALE, Paris (FR); UNIVERSITE PARIS CITE, Paris (FR); ASSISTANCE PUBLIQUE—HOPITAUX DE PARIS, Paris (FR)

(72) Inventors: Ros-Kiri Ing, Ivry sur Seine (FR); Mathias Fink, Meudon (FR); Thomas Similowski, Issy-les-Moulineaux (FR)

(73) Assignees: ECOLE SUPERIEURE DE PHYSIQUE ET DE CHIMIE INDUSTRIELLES DE LA VILLE DE PARIS, Paris (FR); SORBONNE UNIVERSITE INSTITUT NATIONAL DE LA SANTE ET DE LA RECHERCHE MEDICALE, Paris (FR); UNIVERSITE PARIS CITE, Paris (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 317 days.

(21) Appl. No.: 18/555,145

(22) PCT Filed: Apr. 15, 2022

(86) PCT No.: PCT/EP2022/060183
§ 371 (c)(1),
(2) Date: Oct. 12, 2023

(87) PCT Pub. No.: WO2022/219190
PCT Pub. Date: Oct. 20, 2022

(65) Prior Publication Data

US 2024/0188844 A1 Jun. 13, 2024

(30) Foreign Application Priority Data

Apr. 16, 2021 (FR) ...................................... 2103989

(51) Int. Cl.
*A61B 5/08* (2006.01)
*A61B 5/00* (2006.01)

(52) U.S. Cl.
CPC .............. *A61B 5/08* (2013.01); *A61B 5/0051* (2013.01); *A61B 5/0077* (2013.01); *A61B 5/4848* (2013.01); *A61B 2562/0204* (2013.01)

(58) Field of Classification Search
CPC ....... A61B 5/08; A61B 5/0051; A61B 5/0077; A61B 5/4848; A61B 2562/0204
See application file for complete search history.

(56) References Cited

U.S. PATENT DOCUMENTS 6,443,907 B1 * 9/2002 Mansy ..................... A61B 7/04 600/529
2006/0243280 A1 11/2006 Caro

OTHER PUBLICATIONS

Peng et al., Ying, "Sound transmission in the chest under surface excitation: an experimental and computational study with diagnostic applications", Medical and Biological Engineering and Computing., [Online] vol. 52, No. 8, (Aug. 1, 2014), pp. 695-706.
French Search Report issued in corresponding French Application No. 2103989, dated Dec. 23, 2021, p. 1, National Institute of Industrial Property, Paris, France.
Official Letter issued in corresponding European Application No. 22 723 389.7, dated Mar. 12, 2026, pp. 1-6.

* cited by examiner

*Primary Examiner* — Eric F Winakur
(74) *Attorney, Agent, or Firm* — HAUPTMAN HAM, LLP

(57) ABSTRACT

The invention relates to a method for characterizing the vibration of a surface of the chest of an individual, said method including generating an incident vibration of the respiratory system of the individual, said incident vibration having at least one frequency from 20 Hz to 5000 Hz, to obtain resultant vibrations at a surface S of the chest of the individual, said surface S having a surface area of at least 10 $cm^2$ and being characterized by a plurality of points Pi, and measuring the oscillation of each point Pi using a measuring device and obtaining the signal $Sp_i$ of the resultant vibration at each of the points Pi, said measuring device being arranged at a distance from the chest of said individual, and characterizing each signal Spi at the frequenc(y/ies) of the signal $Sp_r$.

17 Claims, 5 Drawing Sheets

[Fig. 1]
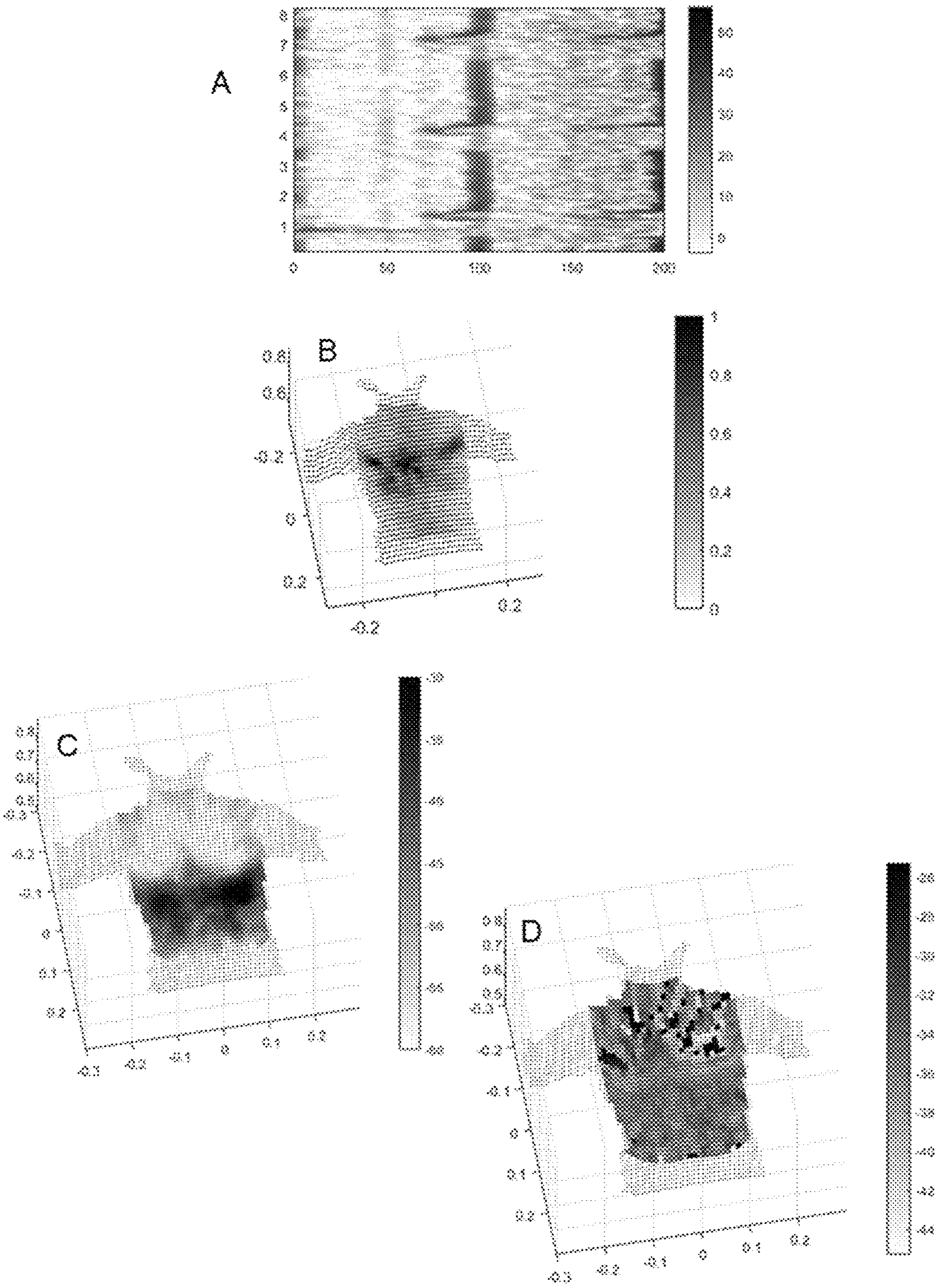

[Fig.2]
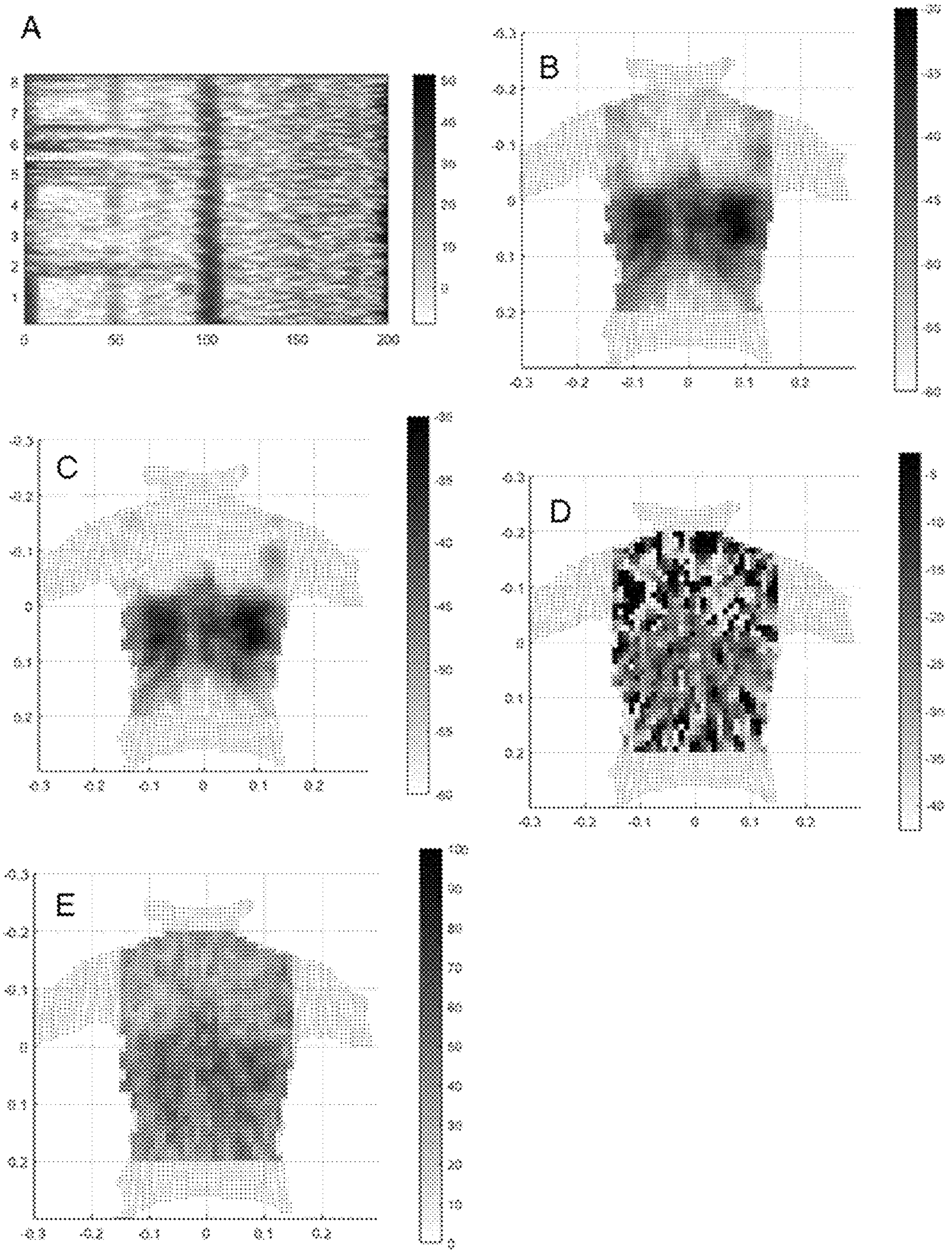

[Fig. 3]
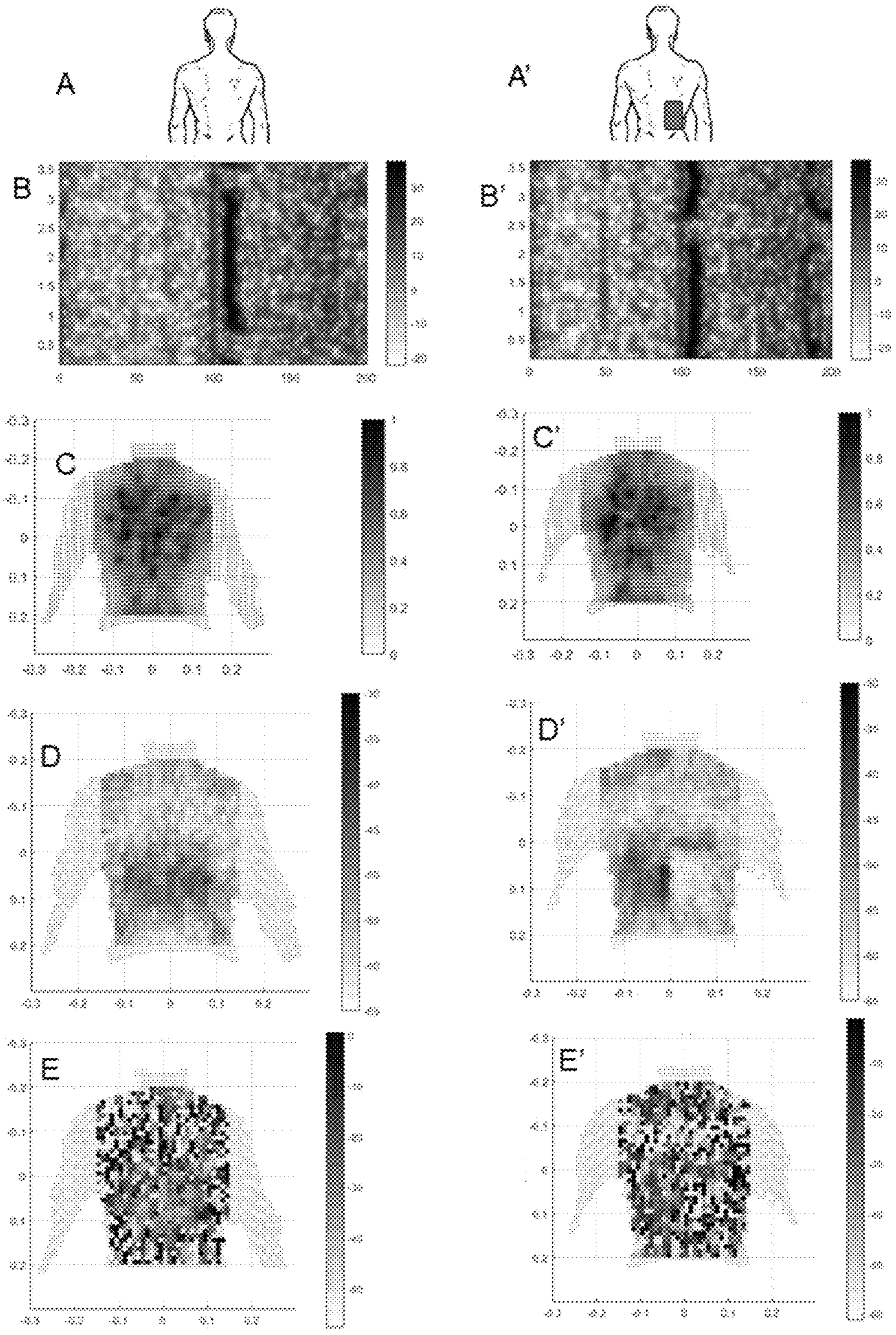

[Fig.4a]
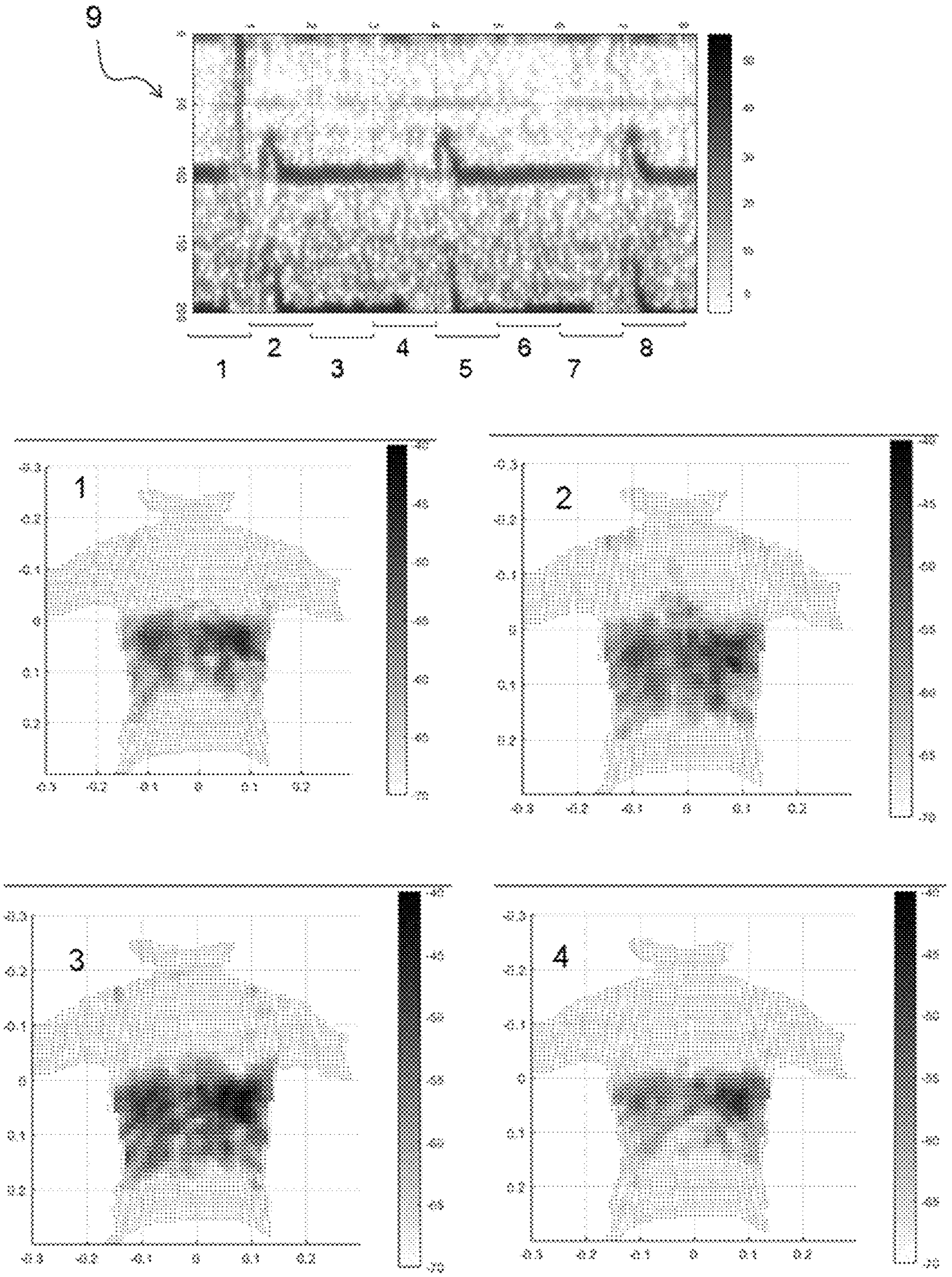

[Fig.4b]
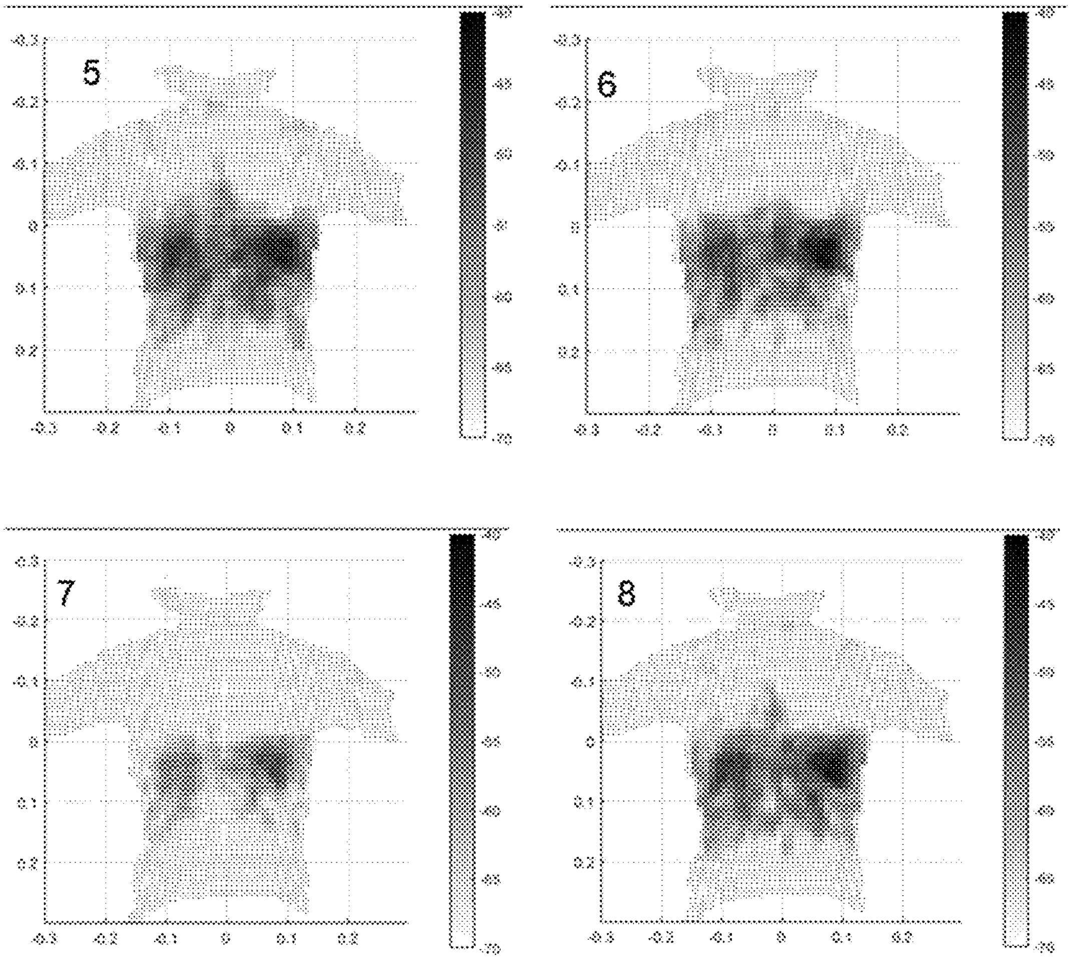

METHOD FOR CHARACTERIZING THE VIBRATION OF A SURFACE

The present application is a U.S. National Phase of International Application Number PCT/EP2022/060183, filed Apr. 15, 2022, which claims priority to French Application No. 2103989, filed Apr. 16, 2021.

DOMAIN OF THE INVENTION

The invention relates to a method for characterizing the vibration of a surface, in particular a surface of the chest of an individual.

TECHNOLOGICAL BACKGROUND

Nowadays, the examination of the thorax practiced by doctors in the context of a respiratory disease takes place in two stages: visual observation at first, then examination of the transmission of vibrations and sounds.

Visual observation comprises searching for an increase in the respiratory rate or a modification of the "ventilatory profile", i.e. the respective duration of inspiration and expiration, and looking for "paradoxical abdominal breathing", i.e. an abdominal deflation on inspiration when one should observe an expansion synchronous with that of the thorax.

The examination of the transmission of the vibrations and of the sounds at the thorax corresponds to the examination of the "vocal fremitus" (tactile) which consists in palpating the thorax wall to detect changes in the intensity of the vibrations generated by some vocalizations or a constant voice, and thus identify a pathology affecting the underlying pulmonary system. For example, the influence of pleurisy on the inhomogeneity of the vocal vibrations reaching the surface of the thorax has been observed. This examination may be carried out in two manners.

This may consist of a manual examination where the doctor places his hands flat on the thorax, asks the patient to pronounce the number "thirty-three" and analyzes the vibrations produced by the voice at the thorax. Then, the doctor places a first hand flat with fingers apart on the thorax of the patient, with the second hand he hits the thorax with his fingers and analyzes the vibrations produced in response using the fingers of the first hand.

The second possible examination is auscultation, using a stethoscope placed on the thorax of a patient, of the sound produced by the circulation of air in the bronchi and lungs of the patient, and the search for abnormal noises.

In the context of the COVID19 disease, the examination of the thorax provides a first approach before a final diagnosis by observing hyperventilation and detecting pulmonary condensations using percussion or auscultation. Nonetheless, this examination has some limitations because it highlights only very flagrant anomalies. In addition, this examination is very dependent on the experience of the observer and does not allow any recording, transmission or subsequent re-analysis of the data. Besides, the ventilatory profile of an individual is a fine and easy to disturb phenomenon. The mere touch of the hand of the doctor or of the stethoscope could affect the results of the examination.

To overcome these drawbacks, the doctor may resort to scanner thorax imaging. This examination allows completing the data of the clinical examination, and in particular visualizing images of "frosted glass" and "condensations" in patients suspected of suffering from infection by the COVID19.

Nonetheless, a scanner imager is extremely expensive, which results in accessibility problems for patients. This accessibility problem results in problems relating to patient transport logistics in the context of the COVID19, which in addition occurs in a context of high contagion. Furthermore, such an examination cannot be repeated frequently, in particular because of the irradiation of the patient involved thereby.

The document US2010298740 describes a system for acoustic measurement of vibration of the skin of a patient by vibration sensors. Nonetheless, such a system allows detecting only very flagrant anomalies, and requires contact of the sensors with the skin of the patient. Contact with the patient could endanger the doctor, in particular in the context of the COVID19 disease, and could affect the results of the examination, like in the context of a stethoscope and of the hand of the doctor.

In particular, one objective of the invention is to overcome these drawbacks of the prior art.

More particularly, one objective of the invention is to provide a method for the fine detection and characterization of vibrations at the surface of the body of an individual without contact with said individual.

SUMMARY

To this end, an object of the invention is a method for characterizing the vibration of a surface of the chest of an individual, in particular in order to establish a diagnosis of a pathology affecting the respiratory system, said method comprising:

a) generating an incident vibration of the respiratory system of the individual, said incident vibration being characterized by a signal $Sp_r$ having at least one frequency from 20 Hz to 5000 Hz, to obtain resultant vibrations at a surface S of the chest of the individual following the propagation of the incident vibration from the respiratory system up to the surface S, said surface S having a surface area of at least 10 $cm^2$ and being characterized by a plurality of points Pi, b) measuring the oscillation of each point Pi using a measuring device and obtaining the signal $Sp_i$ of the resultant vibration at each of the points Pi, said measuring device being arranged at a distance from the chest of said individual, and c) characterizing each signal $Sp_i$ at the frequenc(y/ies) of the signal $Sp_r$:

through the analysis over a given time of at least one parameter p of the signal $Sp_i$ of each point Pi, and/or through the analysis of the dynamics of evolution over a given time of at least one parameter p of the signal $Sp_i$ of each point Pi.

The Inventors have unexpectedly discovered that it was possible to obtain accurate and relevant data for establishing a diagnosis of a disease affecting the respiratory system of an individual, with any contact with said individual and without exposing the patient/individual to radiations. This is made possible by the generation of an incident vibration at his respiratory system and the study of the transformation of this vibration following propagation thereof up to a surface of the chest of the individual. The method according to the invention enables a complete study of the chest of the individual by establishing two or three-dimensional (2D or 3D) vibratory maps on which one or more parameter(s) p of the resultant vibrations or the dynamics of evolution of these parameters may be illustrated.

By "individual", it should be understood in the invention a mammal, in particular a human.

By "chest", it should be understood in the invention the upper front, rear and lateral portion of the body of an individual starting from the waist, or above the lower limbs, and up to the top of the neck, excluding the upper limbs. Thus, the chest includes the abdominal portion, the thoracic portion and the neck of an individual.

By "respiratory system", it should be understood in the invention any organ belonging to the respiratory system, in particular the larynx, the trachea, the main, segmental and lobar bronchi, the alveoli, the bronchioles, the right and left lungs and the diaphragm.

By "pathology affecting the respiratory system", it should be understood any pathology altering the structure and/or the operation of the respiratory system. These pathologies include respiratory pathologies as such as well as cardiac and neuromuscular pathologies affecting the respiratory system.

Step a)

The first step of the method of the invention consists in generation an incident vibration at the respiratory system. The vibration of the respiratory system is forced at one or more determined frequenc(y/ies).

The incident vibration is characterized by a signal $Sp_r$ having at least one frequency from 20 Hz to 5000 Hz, in particular from 40 Hz to 2500 Hz, in particular from 60 Hz to 1000 Hz. Since the frequency profile of the incident vibration corresponds to that which is studied for the resultant vibrations at the surface of the chest, a lower limit of 60 Hz and more is preferred. Indeed, such a low limit allows substantially reducing the parasitic vibrations due to the self-induced vibration of some portions of the body, such as the heart, the blood network, the muscles, etc. . . . .

The frequency profile of the incident vibration may be static or evolve over time. In particular, when the frequency profile evolves over time, the signal $Sp_r$ may have a unique frequency which is modified over time, in particular at regular intervals. Alternatively, the signal $Sp_r$ may have several frequencies each could be modified over time, in particular at regular intervals.

A multi-frequency incident vibration allows refining the analysis of the resultant vibrations and therefore providing more relevant data in order to establish a diagnosis. Indeed, some pathologies are more sensitive to a particular range of frequencies, and generating more frequencies thus allows covering more pathologies.

The frequency range of the incident vibration used in the invention corresponds to that of a human voice. In this manner, the incident vibration may be generated either by a device or by the individual himself, for example by vocalizations.

In particular, the incident vibration may be generated by:

i) a device generating vibrations in an acoustic tube, in particular whose tip is inserted into the oral cavity of said individual, or ii) a vibrating device arranged against a surface $S_g$ of the body of the individual, in particular of the chest, the surfaces $S_g$ and S being opposite one another with respect to the chest of the individual, or iii) a vibration of the vocal cords of said individual.

In the first case i), said device used may consist of any means generating a vibration and in particular a loudspeaker or a compressor. The generated vibration passes throughout an acoustic tube so that it is conveyed up to the respiratory system. The tip of the acoustic tube is inserted into the oral cavity of the individual, or else into the trachea of the latter.

This system is particularly advantageous in the case where the individual is not capable of generating sounds, or generates sounds with an amplitude that is too low for an accurate study of the resultant vibrations at the surface of the chest. Furthermore, this system has the advantage of generating a vibration at one or more determined frequenc(y/ies), and distributing it directly to the respiratory system thanks to the acoustic tube. The incident vibration thus generated by the device is barely transformed when it reaches the respiratory system and is almost identical to that of the respiratory system. Hence, the resultant vibrations are barely, and possibly not, parasitized and their analysis is directly relevant.

In the second case ii), said used device may also consist of any means generating a vibration, and in particular a loudspeaker, a vibrating pot or a pneumatic hammer. In this case, the incident vibration will start from the surface $S_g$, propagate through the body, cross the respiratory system, until reaching the surface S, possibly opposite thereto.

This system is also well suited in the case where the individual is not capable of generating sounds, or generates sounds with an amplitude that is too low for an accurate study of the resultant vibrations at the surface of the chest. This system has the advantage of generating a vibration at one or more determined frequenc(y/ies). In this case, the obtained resultant vibrations are the product of a double transformation: the transformation of the generated vibration up to the respiratory system and the transformation of the incident vibration (that originating from the respiratory system) up to the surface of the chest resulting in the resultant vibrations. Hence, this system involves interference due to the first transformation, and in particular possible processing of the resultant vibrations to suppress this interference.

In the third case iii), it is the individual himself who will generate the vibration of the respiratory system, by vibrating his vocal cords. This alternative has the advantage of requiring no ancillary equipment, which reduces the implementation costs of the invention. The vibration of the vocal cords of the individual may be a simple or complex vocalization, singing or talking. Like the use of an acoustic tube, this aspect of the invention has the advantage of generating a vibration that is directly distributed to the respiratory system. Thus, the generated vibrations and the incident vibration are almost identical, and even identical, and the resultant vibrations are merely the result of the transformation of the incident vibration from the respiratory system up to the surface of the chest. Hence, the resultant vibrations are barely parasitized and their analysis is simplified and directly relevant.

By "simple vocalization", it should be understood in the invention a monotonic sound pronounced by the individual, such as the continuous pronunciation of the phoneme "A", of any other vowel. Therefore, a simple vocalizations has a narrow frequency band, in the range of 4 Hz to 10 Hz, centered on the fundamental frequency.

By "complex vocalization", it should be understood in the invention a shaded sound, such as the pronunciation of the word "thirty-three". A complex vocalization then has a wider frequency band, larger than 10 Hz, centered on the fundamental frequency.

Singing and talking correspond to a shaded sound.

In general, the fundamental is around 100 Hz for a man and 150 Hz for a woman.

For the remainder of the method, the retained frequency band is that around the fundamental, as will be seen later on.

Unlike the previous two cases i) and ii), in the third case iii) the signal $Sp_r$ of the incident vibration is not known and should be determined. This determination may be carried out by any means. In particular, obtaining the signal $Sp_r$ of the incident vibration during step b) is carried out by measuring the sound coming out of the mouth of the patient/individual, in particular using at least one microphone, or the vibration of the lips or the trachea of the patient/individual, in particular using the measuring device used in step b).

When one or more microphone(s) is/are used, these may for example be arranged around the mouth of the individual, in particular in front of his mouth. Alternatively or complementarily, the microphone(s) may be arranged at the measurement device or else correspond to those used for measuring the oscillations of the points Pi. The microphone(s) may be topped with an exponential horn in order to increase their directivity and their sensitivity. In particular, the aperture of the microphone(s) is at least equal to 0.5 mm. Where necessary, a deflector may be positioned in front of the mouth of the individual to attenuate the sound waves propagating towards the microphone(s) and thus avoid saturation thereof.

When it is the vibration of the lips or of the trachea that is analyzed, the latter may be determined using the different methods mentioned below to measure the oscillation of the points Pi.

Once the incident vibration is generated, the latter will propagate throughout the entire respiratory system until reaching the surface of the chest in the form of resultant vibrations. During its travel, the incident vibration will be transformed according to the crossed different media. In particular, its amplitude could be modified. The celerity of the vibration could also be affected and a delay or a phase shift between the resultant vibration and the incident vibration then appears. Hence, the incident vibration will be decomposed into a multitude of resultant vibrations with the different characteristics, each resultant vibration being characteristic of the portion of the respiratory system that the incident vibration will have crossed. Thus, the study of these resultant vibrations provides a wealth of information on the state of the crossed media (dense, soft, presence of recesses, etc.) enabling the establishment of a diagnosis.

To study these resultant vibrations at the chest of the individual, a given surface S of the chest of the individual is selected. This surface S has a surface area of at least 10 $cm^2$ and is characterized by a plurality of points Pi.

In particular, the surface S covers the portion of the chest of interest to establish a diagnosis, i.e. it covers the portion of the respiratory system for which the resultant vibrations are to be studied. Thus, the surface area of the surface S is adapted to the desired study. In particular, this surface may correspond to the surface of the front portion of the thorax, to that of the rear portion, to those of either one of the lateral portions of the thorax, to that of the front or rear portion of the neck, to that of the front or back portion of the abdomen, or to any combination of these surfaces. The surface S may also correspond to the entire surface of the chest of the individual.

The surface S may be composed of one or more discontinuous surface(s). To this end, the surface S may for example correspond to that of the front portion of the neck and to that of the front portion of the thorax covering the right lung.

Each point Pi of the surface S shows a point of the surface of the chest where the signal $Sp_i$ of a resultant vibration will be studied. The more points Pi there are to define this surface S, the closer to each other they will be, and the more accurate the study of the resultant vibrations will be. To this end, the surface S may comprise at least 5 points Pi per 10 $cm^2$, in particular at least 10 points Pi per 10 $cm^2$.

Step b)

The determination of the signal Spi at each point Pi is carried out by measuring the oscillation of the surface of the chest at each point Pi.

Advantageously, the measuring device is arranged at a distance from the individual, and its use does not involve any direct contact with the individual. This aspect of the invention is particularly interesting in the context of an infectious pathology such as the COVID19, where any contact with the patient could lead to an infection of the operator by the patient carrying the agent responsible for the pathology.

To measure the oscillation at each point Pi, the measuring device used in the invention can illuminate each point Pi with waves, then analyze the signal of the waves reflected on the surface S. In this case, each signal $Sp_i$ is a track formation signal. Alternatively, the oscillation at each point Pi may be determined by capturing successive images. In particular, the measurement of the oscillation of each point Pi in step b) is carried out by means of the reflection of ultrasonic waves on said surface S, by means of the reflection of electromagnetic waves on said surface S or by capturing successive images of said surface S.

When the oscillation of each point Pi is measured by means of the reflection of ultrasonic waves, the measuring device may comprise an array of ultrasonic wave emitter transducers and an array of ultrasonic wave receiver transducers (or microphones). In particular, the measuring device may be that described in the document WO2018015638. Furthermore, the measuring device may comprise a 3D camera which also outputs a 3D image corresponding to the x y z coordinates in the point space, in particular points Pi, of a surface of the chest, in particular the surface S, of the individual. In particular, this 3D camera allows positioning said surface at a desired distance from the measuring device or to complete the data gathered in the context of the diagnosis of a pulmonary pathology, for example for individuals suffering from chronic obstructive pulmonary disease (COPD).

In particular, the ultrasonic receiver transducers may be used to obtain the signal $Sp_r$ of the incident vibration by measuring the sound coming out of the mouth of the patient/individual, as seen hereinabove.

The determination of the signals Spi in the context of the reflection of ultrasonic waves may be carried out by the method described in the document WO2018015638.

When the oscillation of each point Pi is measured by means of the reflection of electromagnetic waves, the measuring device may be a radar or laser system.

According to an embodiment of the invention, the measuring device carries out a series of measurements at a rate higher than at least twice the value of the highest frequency of the signal $Sp_r$. In particular, in the case where the generation of the incident vibration is carried out by the vibration of the vocal cords of the individual, the rate may be higher than at least twice the frequency of the fundamental. For example, the rate may amount to at least 300 measurements per second, in particular at least 500 measurements per second, in particular at least 600 measurements per second.

The duration of the measurement of the oscillation of each point Pi corresponds at least to that of the duration of generation of the incident vibration. Afterwards, the data may be segmented over shorter durations when it is the evolution of the dynamics of at least one parameter p which is studied.

In particular, the measurement of the oscillations at each point Pi may begin upstream of the generation of the incident vibration, so as to observe the modifications of oscillation of the points Pi generated by the apparition of the resultant vibrations.

When the oscillation of each point Pi is measured by means of the reflection of ultrasonic waves, the points Pi (and their signals) having a too low coherent reflectivity, in particular a coherent reflectivity lower than 0.1 may be excluded from the remainder of the method. The coherent reflectivity parameter is representative of the error of determination of the speed of movement of the surface S. To obtain the coherent reflectivity of each point Pi of the surface S, all of the points Pi may be illuminated under default circumstances, i.e. with no incident vibration. Then, for each point Pi, the signal s(t) measured over a time t may be correlated with that of the same point s'(t) measured over a subsequent time t+Δt. The signals s(t) and s'(t) are measured, for example, over a time period of 2 milliseconds. At is short, in the range of one millisecond or less. Thus, in theory, these signals are almost identical and only a short time offset t separates them.

The coherent reflectivity may be calculated as follows:

1—calculating the Fourier transforms of the signals s(t) and s'(t), i.e. S(f) and S'(f)

2—correlating the two signals s(t) and s'(t), namely the product S(f)·S'(f)*

3—calculating the coherent reflectivity by integrating the real part of the product over the operating frequency band of the measuring device, in particular from 30 kHz to 60 kHz.

Step c)

This step corresponds to the determination of the transformations undergone by the incident vibration, to detect anomalies. To this end, the resultant vibrations at each point Pi are analyzed at the frequenc(y/ies) of the incident vibration. Indeed, the resultant vibration measured at each point Pi is the sum of multiple vibrations originating from various portions of the body. To characterize the p parameters of the signals $Sp_i$ in a relevant manner, the data relating to the frequenc(y/ies) not corresponding to those of the incident vibration should be excluded. More particularly, one or more parameter(s) p of the signals $Sp_i$ is/are analyzed. By "parameter p", it should be understood in the invention the amplitude of a signal $Sp_i$, a delay or a phase shift or the level of correlation of the signal $Sp_i$ with respect to the signal $Sp_r$ of the incident vibration. In particular, the amplitude of a signal $Sp_i$ may be correlated with that of the signal $Sp_r$ of the incident vibration.

When the incident vibration has been generated by the vibration of the vocal cords of the individual, it is possible to choose to use only one fraction of the frequencies of the signal $Sp_r$ for the analysis of the signals $Sp_i$. In particular, the frequency band used in step c) is around the fundamental. In particular, the frequencies of the incident vibration used during step c) correspond to a band of at most 150 Hz around the fundamental frequency of the incident vibration. In particular, the frequency band is at most 100 Hz, in particular at most 60 Hz, for example at most 40 Hz. The frequency band may be centered on the fundamental frequency.

The analysis of the parameters p of the signals $Sp_i$ may be compared at regular intervals. Indeed, the Inventors have unexpectedly discovered that the evolution over time of the parameters p of the signals $Sp_i$ provide very relevant data for establishing a diagnosis. Indeed, these data allow establishing the dynamics of propagation of the incident vibration.

Advantageously, the data relating to the analyzed parameters p may be distributed on a two-dimensional, and possibly three-dimensional, vibration map. In particular, the dimensions of these maps may represent the special distribution (2D or 3D) of the points Pi therebetween. A color may be assigned to each point Pi according to the value of the analyzed parameter(s) p. Thus, the established vibration map allows identifying very easily areas and values of interest, from which a diagnosis will be established, in particular using a reference vibration map. This reference vibration map may be a map established from a sample of several individuals, in particular healthy or sick individuals, or a map previously established for the individual, in particular before his illness.

In particular, the or one of the parameters p is the amplitude of the signal $Sp_i$ of the resultant vibration. These data are useful for determining which type of medium (dense, soft) the incident vibration has crossed. It should be noted that these amplitude data are raw data which may be parasitized by oscillation measurement noise. One manner for reducing the noise in the case of a measurement by reflection of ultrasonic or electromagnetic waves is to homogeneously illuminate the surface S.

In particular, the or one of the parameters p may be the amplitude of the signal $Sp_i$ of the resultant vibration correlated with the incident vibration. In this case, step b), or step c), comprises for each point Pi the correlation, at the frequenc(y/ies) of the signal $Sp_r$, of the signal $Sp_i$ with the amplitude-normalized signal $Sp_r$ and the determination of the amplitude of the signal of the resultant vibration correlated with the incident vibration. Advantageously, the obtained data are less parasitized by the noise, and therefore more easily exploitable.

These data may be obtained through the following steps:

1—calculating the Fourier transforms of the signal $Sp_r$ and of the signal Spi for each point Pi, which will be denoted $Sp_r(f)$ and $Sp_i(f)$, 2—dividing the complex spectrum of $Sp_r(f)$ by its modulus: $Sp_r(f)/|Sp_r(f)|$, 3—selecting the frequency component(s) of interest, their number amounting to M components, and 4—multiplying the M frequency components of $Sp_r(f)/|Sp_r(f)|$ by the M frequency components of $Sp_i(f)$ (excluding the zero values) then the real part of the product is summed. Optionally, the result is divided by M in order to obtain a normalized amplitude with respect to the number of frequencies.

In particular again, the or one of the parameters p is a delay or a phase shift of the signal $Sp_i$ of the resultant vibration with respect to the signal $Sp_r$ of the incident vibration. In this case, step b), or step c), comprises for each point Pi the correlation of the signal $Sp_i$, in particular amplitude-normalized, at the frequenc(y/ies) of the signal $Sp_r$, with the signal $Sp_r$, in particular amplitude-normalized, and the determination of the delay or the phase shift with respect to the incident vibration at each point Pi. Such data reflect a modification of the celerity of the incident vibration, and may indicate the characteristic celerity of the incident vibration in the crossed media.

The data relating to the delay may be obtained using the following steps:

1—calculating the Fourier transforms of the signal $Sp_r$ and of the signal $Sp_i$ for each point Pi, which will be denoted $Sp_r(f)$ and $Sp_i(f)$, 2—dividing the complex spectra of $Sp_r(f)$ and $Sp_i(f)$ by their respective modulus: $Sp_r(f)/|Sp_r(f)|$ and $Sp_i(f)/|Sp_i(f)|$ in order to obtain spectra normalized in amplitude at 1, 3—selecting the frequency component(s) of interest, their number amounting to M components, 4—multiplying the M frequency components of $Sp_r(f)/|Sp_r(f)|$ by the M frequency components of $Sp_i(f)/|Sp_i(f)|$ (excluding the zero values) then performing an inverse Fourier transform, and 5—searching, afterwards, for the temporal location of the maximum of the intercorrelation. A maximum located at the time origin indicates that the signals are not delayed with respect to one another. A maximum not centered on 0 indicates that one signal is delayed with respect to the other.

The data relating to the phase shift may be obtained using the following steps:

1—calculating the Fourier transforms of the signal $Sp_r$ and of the signal $Sp_i$ for each point Pi, which will be denoted $Sp_r(f)$ and $Sp_i(f)$, 2—selecting the frequency component(s) of interest, their number amounting to M components, and 3—subtracting the phase of each complex spectrum from the M frequency components: $\arg(Sp_i(f))-\arg(Sp_r(f))$.

In particular, the or one of the parameters p is the level of correlation with the incident vibration. In this case, step b), or step c), comprises for each point Pi the correlation, at the frequenc(y/ies) of the signal $Sp_r$, of the amplitude-normalized signal $Sp_i$ with the amplitude-normalized signal $Sp_r$ and the determination of the percentage of correlation with the incident vibration at each point Pi.

These data may be obtained through the following steps:

1—calculating the Fourier transforms of the signal $Sp_r$ and of the signal $Sp_i$ for each point Pi, which will be denoted $Sp_r(f)$ and $Sp_i(f)$, 2—dividing the complex spectra of $Sp_r(f)$ and $Sp_i(f)$ by their respective modulus: $Sp_r(f)/|Sp_r(f)|$ and $Sp_i(f)/|Sp_i(f)|$ in order to obtain spectra normalized in amplitude at 1, 3—selecting the frequency component(s) of interest, their number amounting to M components, and 4—multiplying the M frequency components of $Sp_r(f)/|Sp_r(f)|$ by the M frequency components of $Sp_i(f)/|Sp_i(f)|$ (without the possible zero values), then the real part of the product is summed, and the result is multiplied by M. An intercorrelation amounting to 1 means that the phases of the signals $Sp_i$ and $Sp_r$ are 100% identical.

In particular, the dynamics of evolution over a given time of at least one parameter p of the signal $SP_i$ of each point Pi is analysed by the identical sequential division over time of the signal $Sp_r$ and of each signal $Sp_i$ and identical between the signal $Sp_r$ and each signal $Sp_i$, then by the analysis of at least one parameter p in each sequence of a signal $Sp_i$ and the comparison of the result obtained between each sequence for each signal $Sp_i$.

Following the characterization of each signal $Sp_i$, said at least one analyzed parameter p may be compared with a reference value $p_{ref}$ of the same nature and/or the evolution of said at least one analyzed parameter p may be compared with a reference evolution $p_{vref}$. The reference value $p_{ref}$ may correspond to a value to be reached, to a value previously obtained at the point Pi for the same individual or else to an average value obtained in a population of individuals for this point Pi, in particular a population of healthy or sick individuals. The reference evolution $p_{vref}$ may correspond to an evolution to be reached, to an evolution obtained beforehand at the point Pi for the same individual or else to an average evolution obtained in a population of individuals for this point Pi, in particular a population of healthy or sick individuals. The result of this comparison allows establishing a diagnosis through the determination of the presence or the absence of a significant discrepancy.

The invention also relates to a method for characterizing the vibration of a surface of the chest of an individual suffering from a pathology affecting at least one organ belonging to the respiratory system, in particular in order to establish a diagnosis of the response to a therapeutic treatment intended for said pulmonary disease, said method comprising:

a) characterizing the signals $Sp_i$ of a plurality of points Pi belonging to a surface S of the individual using the method as defined before, where the surface S covers said at least one organ affected by the pulmonary pathology, and b) comparing said at least one parameter p at each point Pi with a reference value $p_{ref}$ of the same nature and/or comparing the evolution of said parameter p at each point Pi with a reference evolution $p_{vref}$, said reference value $p_{ref}$ corresponding to a value to be reached or to the value of the parameter p at the point Pi as determined beforehand, in particular before taking the therapeutic treatment, said reference evolution $p_{vref}$ corresponding to an evolution to be reached or to the evolution of the parameter p at the point Pi as determined beforehand, in particular before taking the therapeutic treatment.

The result of this comparison allows establishing a diagnosis of response to the treatment.

BRIEF DESCRIPTION OF THE FIGURES

FIG. 1 is a set of figures relating to the characterization of resultant vibrations at the surface of the chest of a subject following a complex vocalization of the phoneme "A", with brief repetitions, pronounced by the subject. FIG. 1A is the spectrogram of the voice around the fundamental of the vocalization pronounced by the subject (x-axis: frequencies in Hz; y-axis: time in seconds). The shade scale is in decibels per Hz. FIG. 1B is a 3D mapping of the points Pi forming the studied surface of the resultant vibrations where for each point Pi its coherent reflectivity of the ultrasonic waves used to measure its oscillation is indicated (x-, y- and z-axis in meters). The shade scale is in an arbitrary unit. FIG. 1C is a 3D mapping of the points Pi forming the studied surface of the resultant vibrations where for each point Pi its amplitude correlated with the voice is indicated. The shade scale is in decibels. FIG. 1D is a 3D mapping of the points Pi forming the studied surface of the resultant vibrations where for each point Pi the delay with respect to the voice is indicated. The shade scale is in number of time samples with an implemented sampling period of 1/500 kHz.

FIG. 2 is a set of figures relating to the characterization of resultant vibrations at the surface of the chest of a subject following a vocalization of the phoneme "A", with a long pronunciation, pronounced by the subject. FIG. 2A is the voice spectrogram around the fundamental of the vocalization pronounced by the subject (x-axis: frequencies in Hz; y-axis: time in seconds). The shade scale is in decibels per Hz. FIG. 2B is a 3D mapping of the points Pi forming the studied surface of the resultant vibrations where for each point Pi its amplitude is indicated. The shade scale is in decibels. FIG. 2C is a 3D mapping of the points Pi forming the studied surface of the resultant vibrations where for each point Pi its amplitude correlated with the voice is indicated. The shade scale is in decibels. FIG. 2D is a 3D mapping of the points Pi forming the studied surface of the resultant vibrations where for each point Pi the delay with respect to the voice is indicated. The shade scale is in number of time samples with an implemented sampling period of 1/500 kHz. FIG. 2E is a 3D mapping of the points Pi forming the studied surface of the resultant vibrations where for each point Pi its level of correlation with the voice is indicated. The shade scale is in percents.

FIG. 3 is a set of figures relating to the detection of an anomaly of resultant vibrations at the surface of the chest of a subject following a simple vocalization of the phoneme "A" pronounced by the subject. FIGS. 3A to 3E relate to a subject in a normal situation, and FIGS. 3A' to 3E' relate to the same subject in a situation where a mask has been stuck over the right lower portion of his chest. FIGS. 3A and 3A' illustrate the surface of the studied subject in both situations. FIGS. 3B and 3B' are the voice spectrograms around the fundamental of the vocalization pronounced by the subject (x-axis: frequencies in Hz; y-axis: time in seconds). The shade scale is in decibels per Hz. FIGS. 3C and 3C' are 3D mappings of the points Pi forming the studied surface of the resultant vibrations where for each point Pi its coherent reflectivity of the ultrasonic waves used to measure its oscillation is indicated (x-, y- and z-axis in meter). The shade scale is in an arbitrary unit. FIGS. 3D and 3D' are 3D mappings of the points Pi forming the studied surface of the resultant vibrations where for each point Pi its amplitude correlated with the voice is indicated. The shade scale is in decibels. FIGS. 3E and 3E are 3D mappings of the points Pi forming the studied surface of the resultant vibrations where for each point Pi the delay with respect to the voice is indicated. The shade scale is in number of time samples with an implemented sampling period of 1/500 kHz.

FIG. 4*a* and FIG. 4*b* are a set of 2D mappings of the points Pi forming the studied surface of the resultant vibrations at the surface of the chest of a subject where, for each point Pi, its amplitude correlated with the voice is indicated. The vocalization of the phoneme "A", repeated briefly, is pronounced by the subject. The element 9 corresponds to the spectrogram of the voice of the subject over a time period slightly longer than 8 seconds (x-axis: frequencies in Hz; y-axis: time in seconds). The shade scale is in decibels per Hz. The elements 1 to 8 show the dynamics of evolution of the amplitude of the signal at each point Pi correlated with the voice. Each element 1 to 8 is a 2D mapping of the points Pi forming the studied surface of the resultant vibrations where for each point Pi its amplitude correlated with the voice is indicated. The shade scale is in decibels. Each element 1 to 8 illustrates the result obtained over different measurement times (1: 0-1 seconds; 2: 1-2 s; 3: 2-3 s; 4: 3-4 s; 5: 4-5 s; 6: 5-6 s; 7: 6-7 s; 8: 7-8 s). The correspondence of the measurement time for each element 1 to 8 with respect to the voice of the subject is shown on the element 9.

DETAILED DESCRIPTION

Examples

Example 1—Obtaining and Studying Vibration Mappings

1. Oscillation Measuring Equipment

The vibration characterization of the chest of an individual has been carried out using an ultrasonic imager. This imager comprises an array of 256 ultrasonic wave emitter transducers (model MA40S4S from Murata) and 256 microphones (model FG-23329 from Knowles) for receiving these waves. This microphone array also enables the reception of the sound emitted by the tested subject. The used ultrasonic frequency band is 30 KHz to 60 kHz. The pre-amplification of the microphones is 40 dB. Each emitter transducer and each microphone is provided with an exponential horn transposing the emission aperture of the emitter transducers to 13 mm and the reception aperture of the microphones to 13 mm. Sampling of the reception signal and of the voice of the tested subject is 600 Hz. In turn, the sampling jitter is less than 10 ns.

2. Vibration Mapping a. Simple Vocalization of a Briefly-Repeated Phoneme

The tested subject is a healthy subject who is asked to pronounce the vocalization of the phoneme "A" repeated briefly. The resultant vibrations are characterized at the surface of his front chest from the waistband to the lower neck.

The spectrogram of the voice of the subject is shown in FIG. 1A. In this figure, one could see the repetition of the vocalization lasting about 2 seconds. One could also see that the frequencies with higher amplitudes are concentrated over the band from 70 Hz to 110 Hz (>30 dB/Hz). Also, the characterization of the resultant vibrations is carried out over this frequency band.

FIG. 1B shows the coherent reflectivity of the ultrasonic waves on the studied surface. The closer the value to 1, the better the reflectivity of the waves will be. A reflectivity higher than 0.1 allows obtaining a good interpretation of the signal received by the microphones. Also, the studied surface has subsequently been restricted to points for which a reflectivity was equal to or higher than 0.1.

The amplitude of the signal of the resultant vibrations correlated with the voice of the subject is shown in FIG. 1C. As one could see, the resultant vibrations have a high amplitude at the thoracic level and a weaker one at the abdomen.

The delay of the signal of the resultant vibrations with respect to the voice is shown in FIG. 2D. This delay is almost zero at the thoracic level.

b. Sustained Vocalization of the Same Phoneme

The tested subject is a healthy subject who is asked to pronounce the continuous and sustained vocalization of the phoneme "A". The resultant vibrations are characterized at the surface of his back chest from the waistband to the lower neck.

The spectrogram of the voice of the subject is shown in FIG. 2A. In this figure, one could see the fundamental (100 Hz) and the beginning of the second harmonic (200 Hz). The characterization of the resultant vibrations is carried out over the band from 95 Hz to 108 Hz.

The (raw) amplitude of the signal of the vibrations is shown in FIG. 2B, and the amplitude of the signal of these resultant vibrations correlated with the voice of the subject is shown in FIG. 2C. As one could see, these figures highlight regions with similar high and low amplitudes. Nonetheless, the results in FIG. 2C show a lower contrast of the vibration amplitudes, and a wider high amplitude region. Thus, the results of FIG. 2C provide finer data to establish a diagnosis.

The delay of the signal of the resultant vibrations with respect to the voice is shown in FIG. 2D, and the level of correlation of the signal of the vibrations with the voice is shown with FIG. 2E.

c. Detection of an Anomaly

In this example, a healthy subject pronounces a simple vocalization of the phoneme "A" in two situations: normal and with a mask stuck over the right lower portion of the back (shown in FIGS. 3A and 3A'). This mask, which is less elastic than the skin, simulates an anomaly since it will cause an abnormal vibration of the area it covers. The resultant vibrations are characterized at the surface of his back chest from the waistband to the lower neck.

FIGS. 3B and 3B' show the spectrogram of the voice of the subject in both situations. As one could expect, these spectrograms are almost identical. The retained frequency band for the normal situation is from 106 Hz to 117 Hz and that one retained for the anomaly situation is from 103 Hz to 114 Hz.

FIGS. 3C and 3C' show the coherent reflectivity of the studied surface. In particular, one could see that the good reflectivity area (>0.1) is equivalent in both situations for the same individual. For the characterization of the resultant vibrations, the studied surface has subsequently been restricted to the points for which a reflectivity was equal to or higher than 0.1.

FIGS. 3D and 3D' show the amplitude of the signal of the vibrations correlated with the voice. One could herein see very neatly that the area covered by the mask has a very low amplitude compared to the same area in the normal situation. Thus, it is demonstrated that the alteration of a vibration area is neatly highlighted in the invention, allowing completing a diagnosis.

FIGS. 3E and 3E' show the delay of the signal of the vibrations with respect to the voice. Herein again, strong differences are observed at the hidden zone. The delay which is almost zero in the normal situation becomes stronger in the case of the mask. Thus, it is also demonstrated that several components of the resultant vibrations are altered by the presence of an anomaly, and neatly highlighted by the method of the invention.

d. Evolution Dynamics

The tested subject is a healthy subject who is asked to pronounce the vocalization of the phoneme "A" repeated briefly. The resultant vibrations are characterized at the surface of his back chest from the waistband to the lower neck.

FIGS. 4*a* and 4*b* show the dynamics of the evolution dynamics of the amplitude of the signal of the resultant vibrations correlated with the voice. One could see in these figures that the amplitude remains very strong in some areas, while it decreases or increases in others over time.

Example 2—Differentiation of Healthy Individuals and Patients Suffering from Chronic Obstructive Pulmonary Disease (COPD)

1. Protocol

The same ultrasonic imager as described in Example 1 is used. This imager further comprises a 3D camera which simultaneously provides a conventional image and a 3D image (x y z of the points of the surface of the chest of a subject in front of the device). The subject is either a healthy individual or a patient suffering from COPD.

The height of the panels of the imager, carrying the array of ultrasonic wave emitter transducers, is adjusted or adapted to the size of the subject by placing his xiphoid appendix at the middle of the measurement area. The dimension of this area is 400 mm high and 300 mm wide.

The subject is positioned facing forward (for a measurement of the cardiac movements) or facing backward (for a measurement of the vibrations of the lungs from a vocalization) at a distance comprised between 600 mm and 700 mm, again thanks to the 3D camera.

In the context of a measurement of the cardiac movements, the subject is asked to hold his breath with his lungs full. Afterwards, the subject is asked to perform a series of ten flexions before the measurement in order to increase the amplitude of the cardiac vibrations.

In the context of a measurement of the vibrations of the lungs, the subject is asked to inflate his lungs in order to perform a vocalization.

In these two contexts, the concept of full lungs is achieved by means of a spirometry test repeated three times in order to assess the inspiratory capacity of the subject. These tests aim to train the subject to have the same value of inspiratory capacity three times in a row within a 5% margin, thus when the subject appears in front of the imager, the subject is asked to inflate his lungs to the maximum of their capacities (like in the spirometry test) before beginning vocalization or holding his breath. This manipulation allows normalizing the volume of air in the lungs of the subjects.

Once the subject has his lungs full of air, the subject is given a starting signal for the measurement. The data acquisition last between 3 seconds and 10 seconds. It should be noted that with patients suffering from COPD, it is difficult to carry out the measurements beyond 3 seconds. An end signal is given to the subject to stop the maneuver.

In the context of a measurement of the vibrations of the lungs, the subject is asked to perform the experiment 3 times in a row using different vocalizations, each corresponding to the phonemes "A", "O" and "ZE". The interest of using these different phonemes is to excite different portions of the lungs. The subject is also asked to place the arms in a cross-like fashion on the torso and to repeat the same vocalizations.

Based on the observation that, on average, the fundamental frequency of male vocalizations lies between 100 Hz and 150 Hz and that of female vocalizations between 200 Hz and 300 Hz, the acquisition frequency of the imager is set at 600 ips (images per second) for men and 1000 fps for women.

The invention claimed is:

1. A method for characterizing the vibration of a surface of the chest of an individual in order to establish a diagnosis of a pathology affecting the respiratory system, said method comprising:

a) generating an incident vibration of the respiratory system of the individual, said incident vibration being characterized by a signal $Sp_r$ having at least one frequency from 20 Hz to 5,000 Hz, to obtain resultant vibrations at a surface S of the chest of the individual following the propagation of the incident vibration from the respiratory system up to the surface S, said surface S having a surface area of at least 10 $cm^2$ and being characterized by a plurality of points Pi, b) measuring the oscillation of each point Pi using a measuring device and obtaining the signal $Sp_i$ of the resultant vibration at each of the points Pi, said measuring device being arranged at a distance from the chest of said individual, and c) characterizing each signal $Sp_i$ at a frequency of the signal $Sp_r$:

through the analysis over a given time of at least one parameter p of the signal $Sp_i$ of each point Pi, and/or through the analysis of the dynamics of evolution over a given time of at least one parameter p of the signal $Sp_i$ of each point Pi, wherein in step a) the incident vibration is generated by a vibration of a vocal cord of said individual or a device generating a vibration in an acoustic tube whose tip is inserted into an oral cavity of said individual.

2. The method according to claim 1, wherein the generation of the incident vibration is carried out by a vocalization of the individual, and wherein the obtaining of the signal $Sp_r$ of the incident vibration during step b) is carried out by measuring the sound coming out of the mouth of the individual, or the vibration of the lips and of the trachea of the individual.

3. The method according to claim 2, wherein the measuring is performed using at least one microphone.

4. The method according to claim 2, wherein the measuring of the vibration of the lips and of the trachea of the individual and the measuring of the sound coming out of the mouth of the individual is performed using the same measuring device.

5. The method according to claim 1, wherein the surface S comprises at least 5 points Pi per 10 $cm^2$.

6. The method according to claim 5, wherein the surface S comprises at least 10 points Pi per 10 $cm^2$.

7. The method according to claim 1, wherein the measurement of the oscillation of each point Pi in step b) is carried out by the reflection of ultrasonic waves on said surface S, by the reflection of electromagnetic waves on said surface S or by successively capturing images of said surface S.

8. The method according to claim 7, wherein the measurement is a series of measurements carried out at a rate of at least 300 measurements per second.

9. The method according to claim 1, wherein in step a) the incident vibration is generated by a vocalization of the individual, and wherein the frequencies of the incident vibration used during step c) correspond to a band of at most 100 Hz around the fundamental frequency of the incident vibration.

10. The method according to claim 9, wherein the frequencies of the incident vibration used during step c) correspond to a band of at most 100 Hz centered on the fundamental frequency of the incident vibration.

11. The method according to claim 1, wherein the or one of the parameters p is the amplitude of the signal $Sp_i$ of the resultant vibration.

12. The method according to claim 1, wherein the or one of the parameters p is the amplitude of the signal $Sp_i$ of the resultant vibration correlated with the incident vibration, and where step c) comprises for each point Pi the correlation of the amplitude-normalized signal $Sp_i$, at a frequency of the signal $Sp_r$, with the amplitude-normalized signal $Sp_r$ and the determination of the amplitude of the signal of the resultant vibration correlated with the incident vibration.

13. The method according to claim 1, wherein the or one of the parameters p is a delay or phase shift of the signal $Sp_i$ of the resultant vibration with respect to the signal $Sp_r$ of the incident vibration, and where step b) comprises for each point Pi correlating, at the a frequency of the signal $Sp_r$, the signal $Sp_i$ with the signal $Sp_r$ and determining the delay or the phase shift with respect to the incident vibration at each point Pi.

14. The method according to claim 13, wherein the signal $Sp_i$ is amplitude-normalized.

15. The method according to claim 9, wherein the signal $Sp_r$ is amplitude-normalized.

16. A method for characterizing the vibration of a surface of the chest of an individual suffering from a pathology affecting at least one organ belonging to the respiratory system in order to establish a diagnosis of the response to a therapeutic treatment intended for said pulmonary disease, said method comprising:

a) characterizing the signals $Sp_i$ of a plurality of points Pi belonging to a surface S of the individual using the method according to claim 1, where the surface S covers said at least one organ affected by the pulmonary pathology, and b) comparing said at least one parameter p at each point Pi with a reference value $p_{ref}$ of the same nature and/or comparing the evolution of said parameter p at each point Pi with a reference evolution $p_{vref}$, said reference value $p_{ref}$ corresponding to a value to be reached or to the value of the parameter p at the point Pi as determined beforehand, said reference evolution $p_{vref}$ corresponding to an evolution to be reached or to the evolution of the parameter p at the point Pi as determined beforehand.

17. The method according to claim 16, wherein the parameter p at the point Pi as determined beforehand is before taking the therapeutic treatment.

* * * * *